United States Patent
Uchida et al.

(10) Patent No.: US 7,696,366 B2
(45) Date of Patent: Apr. 13, 2010

(54) PRODUCTION PROCESS OF BIFUNCTIONAL EPOXY MONOMER BY SELECTIVE OXIDATION OF DIOLEFIN COMPOUND

(75) Inventors: Hiroshi Uchida, Kawasaki (JP); Yuko Sakata, Kawasaki (JP); Ritsuko Hirakawa, Kawasaki (JP); Kazuhiko Sato, Tsukuba (JP); Masanori Ookoshi, Tsukuba (JP)

(73) Assignee: Showa Denko K.K., Tokyo (JP)

( * ) Notice: Subject to any disclaimer, the term of this patent is extended or adjusted under 35 U.S.C. 154(b) by 115 days.

(21) Appl. No.: 11/914,489

(22) PCT Filed: May 16, 2006

(86) PCT No.: PCT/JP2006/310097
§ 371 (c)(1),
(2), (4) Date: Nov. 15, 2007

(87) PCT Pub. No.: WO2006/123814
PCT Pub. Date: Nov. 23, 2006

(65) Prior Publication Data
US 2009/0030217 A1    Jan. 29, 2009

Related U.S. Application Data

(60) Provisional application No. 60/684,576, filed on May 26, 2005.

(30) Foreign Application Priority Data
May 16, 2005    (JP) .............................. 2005-143124

(51) Int. Cl.
*C07D 301/12*    (2006.01)

(52) U.S. Cl. .......................... 549/531; 549/545; 549/546
(58) Field of Classification Search ................. 549/546, 549/531, 545
See application file for complete search history.

(56) References Cited

FOREIGN PATENT DOCUMENTS

| EP | 0 190 609 A2 | | 8/1986 |
|---|---|---|---|
| EP | 0 493 778 A1 | | 7/1992 |
| GB | 788541 | | 1/1958 |
| JP | 5-213919 A | | 8/1993 |
| JP | 2002-155066 | * | 5/2002 |
| JP | 2003-192679 A | | 7/2003 |
| TW | 526215 B | | 4/2003 |
| WO | 93/00338 A2 | | 1/1993 |
| WO | 00/77066 A2 | | 12/2000 |

OTHER PUBLICATIONS

Frostick et al., Journal of the American Chemical Society, 1959, 81, 3350-3356.*

* cited by examiner

*Primary Examiner*—Bernard Dentz
*Assistant Examiner*—David E Gallis
(74) *Attorney, Agent, or Firm*—Sughrue Mion, PLLC

(57) ABSTRACT

There is provided a novel method for producing a bifunctional epoxy monomer which comprises reacting diolefin with a hydrogen peroxide aqueous solution, in the presence of molybdenum or tungsten oxide as a catalyst to selectively epoxidize a double bound at a specific position. The bifunctional epoxy monomers provided by the present invention are substances widely used in various industrial fields such as chemical industry, as materials for resist materials (particularly solder resist materials), and intermediates of agrochemicals and medicines, and various polymers such as plasticizers, adhesives and coating resins.

6 Claims, No Drawings

PRODUCTION PROCESS OF BIFUNCTIONAL EPOXY MONOMER BY SELECTIVE OXIDATION OF DIOLEFIN COMPOUND

CROSS-REFERENCES TO RELATED APPLICATIONS

This application claims benefit under 35 U.S.C. §119(e) to U.S. Provisional Application Ser. No. 60/684,576 filed May 26, 2005.

TECHNICAL FIELD

The present invention relates to a method for epoxidizing diolefin to obtain a bifunctional epoxy monomer having an epoxy group and a double bond in the molecule. The present invention particularly relates to a novel method for producing a bifunctional epoxy monomer which comprises reacting diolefin with a hydrogen peroxide aqueous solution in the presence of an oxide of molybdenum or tungsten as a catalyst to selectively epoxidize a double bond at a specific position. The bifunctional epoxy monomers provided by the present invention are useful materials which can be widely used in various industrial fields such as chemical industry, as materials for resist materials (particularly solder resist materials), intermediates of agrochemicals and medicines, and various polymers such as plasticizers, adhesives and coating resins.

BACKGROUND ART

The technique for selectively epoxidizing one double bond at a specific position of diolefin is of low productivity (low reactivity, low selectivity), and application thereof is often limited to those with structures of some kinds.

Peracids have been conventionally used as selective epoxidizing agents for diolefin (see, for example, Chem. Ber., 1985, 118, 1267-1270). However, in the technique, a large amount of diepoxides are produced as by-products, and equivalent amounts of acids derived from the oxidizing agents are produced, which cause problems such as corrosion of apparatuses.

A selective epoxidizing method of a diolefin using oxone as an oxidizing agent in the presence of a ketone catalyst (for example, see J. Org. Chem., 1998, 63, 2948-2953) has been known. In this reaction, there are problems that a large amount (20 to 30 mol % relative to diolefin) of ketones of catalysts are required, and the reaction conditions such as a pH and a reaction temperature must be strictly controlled in order to prevent reacting oxon from being decomposed.

On the other hand, a hydrogen peroxide solution is cheep, non-corrosive, and environmentally friendly because any by-product is not produced or the by-product is water. It is an excellent oxidizing agent to be used in industry.

As the methods for producing an epoxy compound from an olefin using a hydrogen peroxide solution as an epoxidizing agent, (1) an epoxidizing method with hydrogen peroxide in the presence of quaternary ammonium chloride, phosphoric acids, and a tungsten metal salt {see Kokai (Jpn. Unexamined Patent Publication) 2003-192679 (Patent Publication 1 hereinafter)}; (2) an epoxidizing method with hydrogen peroxide using organic oxorhenium as a catalyst {see Kokai 2001-25665 (Patent Publication 2 hereinafter)}; (3) an epoxidizing method with titanium silicate and hydrogen peroxide (see, for example, Journal of Catalysis, 1993, 140, 71-83); and (4) an epoxidizing method with hydrogen peroxide in the presence of a fluoroalkyl ketone catalyst (see, for example, Chem. Commun., 1999, 263-264) have been known. These methods basically relate to epoxidizing of a monoolefin having sole double bond, and do not indicate selective epoxidizing of diolefin.

With respect to selective epoxidizing of diolefin using a hydrogen peroxide solution as an epoxidizing agent, there are (5) a method for epoxidizing diolefin with hydrogen peroxide in the presence of a catalyst represented by the formula $Q_3XW_4O_{24}$ (in the formula, Q represents a quaternary ammonium cation having carbon atoms up to 70, X represents P or As) (see, for example, Kokai 4-275281); (6) a method for epoxidizing diolefin having a methacrylic acid unit with hydrogen peroxide in the presence of quaternary ammonium chloride, phosphoric acid, and a tungsten compound (see, for example, Tetrahedron, 1992, 48 (24), 5099-5110); (7) a method for epoxidizing diolefin with hydrogen peroxide in the presence of a tungsten and molybdenum polyoxometalate complex {see, for example, Kokai 2002-155066 (Patent Publication 3 hereinafter)}; and (8) a method for epoxidizing diolefin using organic oxorhenium as a catalyst (Angew. Chem. Int. Ed. Engl., 1991, 30(12), 1638-1641). However, in the above method (5), the amount of hydrogen peroxide is less than one equivalent amount relative to one equivalent amount of diolefin, the reaction yields are very poor (32 to 48% relative to the used diolefin), it takes much time and it costs much money for performing separation and purification steps which result in poor productivity. As the catalyst has a surfactant property and a halogenated hydrocarbon such as methylene chloride is required for phase separation after the reaction is complete, it is not environmentally friendly. The above methods (6) and (7) have strict substrate specificity, the substrates in the methods (6) and (7) are limited to diolefins having a methacrylic acid unit and large cycle diolefins having 8 to 20 rings, respectively. Especially in the above method (8), substrate conversion ratio of diolefin is very high, but a large amount of a diol compound of a hydrolysis product from a bifunctional epoxy monomer is produced as a by-product, and the yield of the monoepoxy compound is low. Organic oxorhenium is very expensive, and they are industrially cost ineffective.

Accordingly, a method for selectively producing a bifunctional epoxy monomer in high yield at a low cost from diolefin, under a mild condition, without any use of an organic solvent, by easy operation, has been strongly desired.

[Patent Publication 1] Kokai 2003-192679
[Patent Publication 2] Kokai 2001-25665
[Patent Publication 3] Kokai 2002-155066

SUMMARY OF THE INVENTION

The present invention is directed to providing a novel safe and easy production method of a bifunctional epoxy monomer comprising reacting diolefin with a hydrogen peroxide aqueous solution, under a mild condition, without any use of an organic solvent.

The inventors studied hard to solve the problems, and discovered that if diolefin is reacted with a hydrogen peroxide aqueous solution without any use of an organic solvent, using quaternary ammonium hydrogen sulfate and a Group VI metal compound (molybdenum, tungsten) as a catalyst, a bifunctional epoxy monomer having an epoxy group and a double bond in the molecule is selectively produced in high yield, and completed the present invention.

The present invention relates to a method for producing a bifunctional epoxy monomer comprising reacting diolefin with a hydrogen peroxide aqueous solution in the presence of quaternary ammonium hydrogen sulfate and a catalytic amount of a Group VI metal compound (molybdenum, tungsten), without any use of an organic solvent.

The present invention specifically relates to a method for producing a bifunctional epoxy monomer represented by the following formula (2):

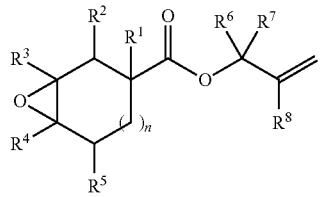
(2)

Wherein n represents an integer of 0 to 2, $R^1$ to $R^8$ each is independently identical or different, and represents a hydrogen atom, a hydroxy group, a halogen atom, a carboxyl group, an alkyl group having 1 to 4 carbon atoms, an alkoxy group having 1 to 4 carbon atoms, a cycloalkyl group having 3 to 7 carbon atoms, an aryl group, an aralkyl group, an acyl group, an acyloxy group, or $R^1$ and $R^2$; $R^1$ and $R^3$; $R^1$ and $R^4$; $R^1$ and $R^5$; $R^2$ and $R^3$; $R^2$ and $R^4$; $R^2$ and $R^5$; $R^3$ and $R^4$; $R^3$ and $R^5$; or $R^4$ and $R^5$ represent a carbon chain bridge having 1 to 3 carbon atoms, and these groups may be independently substituted with an alkyl group having 1 to 4 carbon atoms, an alkoxy group having 1 to 4 carbon atoms, a cycloalkyl group having 3 to 7 carbon atoms, an aryl group, an aralkyl group, a carboxyl group or a halogen atom, the method comprising selectively oxidizing a diolefin compound represented by the following formula (1):

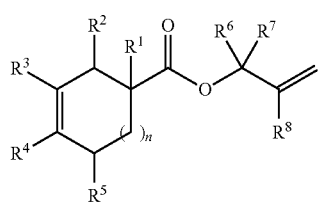
(1)

wherein n represents an integer of 0 to 2, $R^1$ to $R^8$ each is independently identical or different, and represents a hydrogen atom, a hydroxy group, a halogen atom, a carboxyl group, an alkyl group having 1 to 4 carbon atoms, an alkoxy group having 1 to 4 carbon atoms, a cycloalkyl group having 3 to 7 carbon atoms, an aryl group, an aralkyl group, an acyl group, an acyloxy group, or $R^1$ and $R^2$; $R^1$ and $R^3$; $R^1$ and $R^4$; $R^1$ and $R^5$; $R^2$ and $R^3$; $R^2$ and $R^4$; $R^2$ and $R^5$; $R^3$ and $R^4$; $R^3$ and $R^5$; or $R^4$ and $R^5$ represent a carbon chain bridge having 1 to 3 carbon atoms, and these groups may be independently substituted with an alkyl group having 1 to 4 carbon atoms, an alkoxy group having 1 to 4 carbon atoms, a cycloalkyl group having 3 to 7 carbon atoms, an aryl group, an aralkyl group, a carboxyl group or a halogen atom, using an oxidizing agent.

The above-described oxidizing agent may be a hydrogen peroxide aqueous solution.

A Group VI metal compound (molybdenum, tungsten) and quaternary ammonium hydrogen sulfate can be used as a catalyst.

EFFECT OF THE INVENTION

According to the method of the present invention, a bifunctional epoxy monomer, which is useful substance widely used in various industrial fields, such as chemical industry, as materials for resist materials (particularly solder resist materials), intermediates of agrochemicals and medicines, and various polymer materials for plasticizers, adhesives, coating resins, can be produced by reaction of the corresponding diolefin with a hydrogen peroxide solution by easy and safe operation, in high yield, at low cost. The present invention brings great influences to industry. In the method of the present invention, any organic solvent, acids and bases are not used, and the method has an environmentally friendly effect.

DETAILED DESCRIPTION OF THE INVENTION

The diolefin compound of the substrate in the present invention is represented, for example, by the following formula (1):

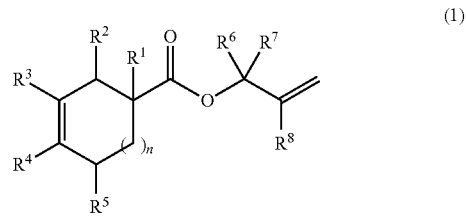
(1)

wherein n represents an integer of 0 to 2, $R^1$ to $R^8$ each is independently identical or different, and represents a hydrogen atom, a hydroxy group, a halogen atom, a carboxyl group, an alkyl group having 1 to 4 carbon atoms, an alkoxy group having 1 to 4 carbon atoms, a cycloalkyl group having 3 to 7 carbon atoms, an aryl group, an aralkyl group, an acyl group, an acyloxy group, or $R^1$ and $R^2$; $R^1$ and $R^3$; $R^1$ and $R^4$; $R^1$ and $R^5$; $R^2$ and $R^3$; $R^2$ and $R^4$; $R^2$ and $R^5$; $R^3$ and $R^4$; $R^3$ and $R^5$; or $R^4$ and $R^5$ represent a carbon chain bridge having 1 to 3 carbon atoms, and these groups may be independently substituted with an alkyl group having 1 to 4 carbon atoms, an alkoxy group having 1 to 4 carbon atoms, a cycloalkyl group having 3 to 7 carbon atoms, an aryl group, an aralkyl group, a carboxyl group or a halogen atom.

More specifically, the diolefin compound of a substrate in the present invention includes 3-cyclopenten-1-carboxylic acid allyl ester, 1-methyl-3-cyclopenten-1-carboxylic acid allyl ester, 3-methyl-3-cyclopenten-1-carboxylic acid allyl ester, 3,4-dimethyl-3-cyclopenten-1-carboxylic acid allyl ester, 3-cyclopenten-1-carboxylic acid-2'-methyl-2'-propenyl ester, 3-cyclopenten-1-carboxylic acid 2'-chloro-2'-propenyl ester, 3-cyclopenten-1-carboxylic acid 2'-bromo-2'-propenyl ester, 3-cyclopenten-1-carboxylic acid 1'-methyl-2'-propenyl ester, 3-cyclopenten-1-carboxylic acid 1'-ethyl-2'-propenyl ester, 3-cyclopenten-1-carboxylic acid 1'-phenyl-2'-propenyl ester, 3-cyclohexen-1-carboxylic acid allyl ester, 1-methyl-3-cyclohexen-1-carboxylic allyl ester, bicyclo[2.2.1]-5-hepten-2-methyl-2-carboxylic acid allyl ester, 3-cyclohexen-1-carboxylic acid 2'-methyl-2'-propenyl ester, 3-cyclohexen-1-carboxylic acid 2'-chloro-2'-propenyl ester, 3-cyclohexen-1-carboxylic acid 2'-bromo-2'-propenyl ester, 3-cyclohexen-1-carboxylic acid 1'-methyl-2'-propenyl ester, 3-cyclohexen-1-carboxylic acid 1'-ethyl-2'-propenyl ester, 3-cyclohexen-1-carboxylic acid 1'-phenyl-2'-propenyl ester, 3-cyclohepten-1-carboxylic acid allyl ester, 1-methyl-3-cyclohepten-1-carboxylic acid allyl ester, 3-methyl-3-cyclohepten-1-carboxylic acid allyl ester, 3,4-dimethyl-3-cyclohepten-1-carboxylic acid allyl ester, 3-cyclohepten-1-carboxylic acid 2'-methyl-2'-propenyl ester, 3-cyclohepten-1-carboxylic acid 2'-chloro-2-propenyl ester, 3-cyclohepten-1-carboxylic acid 2'-bromo-2'-propenyl ester, 3-cyclohepten-1-carboxylic acid 1'-methyl-2'-propenyl ester, 3-cyclohepten-1-carboxylic acid 1'-ethyl-2'-propenyl ester, and 3-cyclohepten-1-carboxylic acid 1'-phenyl-2'-propenyl ester.

The diolefin compound of a substrate in the present invention preferably includes 3-cyclohexen-1-carboxylic acid allyl ester, 1-methyl-3-cyclohexen-1-carboxylic acid allyl ester, bicyclo[2.2.1]-5-hepten-2-methyl-2-carboxylic acid allyl ester, and 3-cyclohexen-1-carboxylic acid 2'-methyl-2'-propenyl ester.

The concentration of a hydrogen peroxide solution used in the method of the present invention is not particularly limited, and reaction proceeds, resulting in diolefin production. The concentration is usually selected from the range of 1 to 80%, preferably 20 to 60%.

The amount of hydrogen peroxide aqueous solution is not limited and reaction proceeds, resulting in diolefin production, depending on the amount. The amount is usually selected from the range of 0.8 to 10.0 equivalent amounts, preferably 1.0 to 3.0 equivalent amounts.

The quaternary ammonium hydrogen sulfate includes tetrahexylammonium hydrogen sulfate, tetraoctylammonium hydrogen sulfate, methyltrioctylammonium hydrogen sulfate, tetrabutylammonium hydrogen sulfate, ethyltrioctylammonium hydrogen sulfate, and cetylpyridinium hydrogen sulfate. Tetrahexyammonium hydrogen sulfate, tetraoctylammonium hydrogen sulfate, and methyltrioctylammonium hydrogen sulfate are preferable. These quaternary ammonium hydrogen sulfates can be used alone or in combination of two or more thereof. The amount thereof is selected from the range 0.0001 to 10 mol %, preferably 0.01 to 5 mol %, relative to diolefin of a substrate.

The Group VI metal compound which is molybdenum, for example, produces molybdic acid anions in water, and includes molybdic acid, molybdenum trioxide, molybdenum trisulfide, molybdenum hexachloride, phosphomolybdic acid, ammonium molybdate, potassium molybdate dihydrate, and sodium molybdate dihydrate. Molybdic acid, molybdenum trioxide, and phosphomolybdic acid are preferable. If it is tungsten, it produces tungsten acid anions in water, and includes tungsten acid, tungsten trioxide, tungsten trisulfide, tungsten hexachloride, phosphotungstic acid, ammonium tungstate, potassium tungstate dihydrate, and sodium tungstate dihydrate. Tungsten acid, tungsten trioxide, phosphotungstic acid and sodium tungstate dihydrate are preferable. These Group VI compounds can be used alone or in combination of two or more compounds. The amount thereof is 0.0001 to 20 mol %, preferably 0.01 to 10 mol %, relative to a diolefin of a substrate. The catalyst of the kind can be modified using an additive such as phosphoric acid, polyphosphoric acid, aminomethylphosphonic acid, or sodium phosphate.

In the production method of the present invention, reaction is usually performed at temperature of 30 to 100° C., preferably 50 to 90° C.

Thus-obtained bifunctional epoxy monomers are compounds represented by the formula (2):

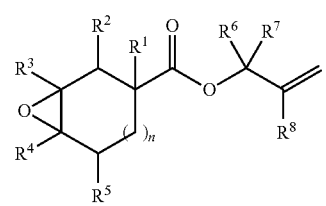

wherein n represents an integer of 0 to 2, $R^1$ to $R^8$ each is independently identical or different, and represents a hydrogen atom, a hydroxy group, a halogen atom, a carboxyl group, an alkyl group having 1 to 4 carbon atoms, an alkoxy group having 1 to 4 carbon atoms, a cycloalkyl group having 3 to 7 carbon atoms, an aryl group, an aralkyl group, an acyl group, an acyloxy group, or $R^1$ and $R^2$; $R^1$ and $R^3$; $R^1$ and $R^4$; $R^1$ and $R^5$; $R^2$ and $R^3$; $R^2$ and $R^4$; $R^2$ and $R^5$; $R^3$ and $R^4$; $R^3$ and $R^5$; or $R^4$ and $R^5$ represent a carbon chain bridge having 1 to 3 carbon atoms, and these groups may be independently substituted with an alkyl group having 1 to 4 carbon atoms, an alkoxy group having 1 to 4 carbon atoms, a cycloalkyl group having 3 to 7 carbon atoms, an aryl group, an aralkyl group, a carboxyl group or a halogen atom.

Examples of the obtained bifunctional epoxy monomers include 3,4-epoxycyclopentan-1-carboxylic acid allyl ester, 1-methyl-3,4-epoxycyclopentan-1-carboxylic acid allyl ester, 3-methyl-3,4-epoxycyclopentan-1-carboxylic acid allyl ester, 3,4-dimethyl-3,4-epoxycyclopentan-1-carboxylic acid allyl ester, 3,4-epoxycyclopentan-1-carboxylic acid 2'-methyl-2'-propenyl ester, 3,4-epoxycyclopentan-1-carboxylic acid 2'-chloro-2'-propenyl ester, 3,4-epoxycyclopentan-1-carboxylic acid 2'-bromo-2'-propenyl ester, 3,4-epoxycyclopentan-1-carboxylic acid 1'-methyl-2'-propenyl, 3,4-epoxycyclopentan-1-carboxylic acid 1'-ethyl-2'-propenyl ester, 3,4-epoxycyclopentan-1-carboxylic acid 1'-phenyl-2'-propenyl ester, 3,4-epoxycyclohexan-1-carboxylic acid allyl ester, 1-methyl-3,4-epoxycyclohexan-1-carboxylic acid allyl ester, 3-oxa[3.2.1.0$^{2,4}$]octan-6-methyl-6-carboxylic acid allyl ester, 3,4-epoxycyclohexan-1-carboxylic acid 2'-methyl-2'-propenyl ester, 3,4-epoxycyclohexan-1-carboxylic acid 2'-chloro-2'-propenyl ester, 3,4-epoxycyclohexan-1-carboxylic acid 2'-bromo-2'-propenyl ester, 3,4-epoxycyclohexan-1-carboxylic acid 1'-methyl-2'-propeyl ester, 3,4-epoxycyclohexan-1-carboxylic acid 1'-ethyl-2'-propenyl ester, 3,4-epoxycyclohexan-1-carboxylic acid 1'-phenyl-2'-propenyl ester, 3,4-epoxycycloheptan-1-carboxylic acid allyl ester, 1-methyl-3,4-epoxycycloheptan-1-carboxylic acid allyl ester, 3-methyl-3,4-epoxycycloheptan-1-carboxylic acid allyl ester, 3,4-dimethyl-3,4-epoxycycloheptan-1-carboxylic acid allyl ester, 3,4-epoxycycloheptan-1-carboxylic acid 2'-methyl-2'-propenyl ester, 3,4-epoxycycloheptan-1-carboxylic acid 2'-chloro-2'-propenyl ester, 3,4-epoxycycloheptan-1-carboxylic acid 2'-bromo-2'-propenyl ester, 3,4-epoxycycloheptan-1-carboyxlic acid 1'-methyl-2'-propenyl ester, 3,4-epoxycycloheptan-1-carboxylic acid 1'-ethyl-2'-propenyl ester, and 3,4-epoxycycloheptan-1-carboyxlic acid 1'-phenyl-2'-propenyl ester. Preferable examples include 3,4-epoxycyclohexan-1-carboxylic acid allyl ester, 1-methyl-3,4-epoxycyclohexan-1-carboxylic acid allyl ester, 3-oxa[3.2.1.0$^{2,4}$]octan-6-methyl-6-carboyxlic acid allyl ester, and 3,4-epoxycyclohexan-1-carboxylic acid 2'-methyl-2'-propenyl ester.

Thus-formed desired bifunctional epoxy monomer can be isolated after the mixture solution has been concentrated, by a general step such as recrystallization, distillation and sublimation.

The present invention will be further specifically explained with the following examples, but it is not limited thereto.

EXAMPLES

Example 1

After $Na_2WO_4.2H_2O$ (500 mg, 1.5 mmol), 40% hydrogen peroxide aqueous solution (7.65 g, 90 mmol), methyltrioctylammonium hydrogen sulfate (260 mg, 0.56 mmol) and 3-cyclohexen-1-carboxylic acid allyl ester (12.5 g, 75 mmol) were mixed, and were reacted at 25° C. for 15 min., the temperature was raised to 70° C., and the mixture was stirred for 3.5 hours. After the reaction was complete, the mixture was cooled to room temperature. Aftertreatment was performed with a sodium thiosulfate saturated aqueous solution, an organic layer was taken out. The obtained solution was determined by gas chromatography, and it was confirmed that the conversion rate of 3-cyclohexen-1-carboxylic acid allyl ester of a starting material was 79%, and the yield of 3,4-epoxycyclohexan-1-carboxylic acid allyl ester of a bifunctional epoxy monomer was 69%. The result that no diepoxides were formed, and monoepoxy selectivity was 100% was obtained.

Example 2

After $Na_2WO_4.2H_2O$ (39.6 mg, 0.12 mmol), 36% hydrogen peroxide aqueous solution (600 mg, 6.3 mmol), methyltrioctylammonium hydrogen sulfate (23.4 mg, 0.05 mmol), aminomethylphosphonic acid (4.5 mg, 0.04 mmol) and 3-cyclohexen-1-carboxylic acid allyl ester (1.00 g, 6 mmol) were mixed, and were reacted at 25° C. for 15 min., the temperature was raised to 70° C., and the mixture was stirred for 3 hours. The same steps as in Example 1 were repeated. It was confirmed that the conversion rate of 3-cyclohexen-1-carboxylic acid allyl ester of a starting material was 89%, and the yield of 3,4-epoxycyclohexan-1-carboxylic acid allyl ester of a bifunctional epoxy monomer was 80%. The result that no diepoxides were formed, and monoepoxy selectivity was 100% was obtained.

Example 3

After $Na_2WO_4.2H_2O$ (26.4 mg, 0.08 mmol), 36% hydrogen peroxide aqueous solution (400 mg, 4.2 mmol), methyltrioctylammonium hydrogen sulfate (15.6 mg, 0.033 mmol), aminomethylphosphonic acid (3.0 mg, 0.027 mmol), and bicycle[2.2.1]-5-hepten-2-methyl-2-carboxylic acid allyl ester (0.79 g, 4 mmol) were mixed, and were reacted at 25° C. for 15 min., the temperature was raised to 70° C., and the mixture was stirred for 3 hours. The same steps as in Example 1 were repeated. It was confirmed that the conversion rate of bicycle[2.2.1]-5-hepten-2-methyl-2-carboxylic acid allyl ester of a starting material was 74%, and the yield of 3-oxa [3.2.1.0$^{2,4}$]octan-6-methyl-6-carboxylic acid allyl ester of a bifunctional epoxy monomer was 70%. The result that no diepoxides were formed, and monoepoxy selectivity was 100% was obtained.

Comparative Example 1

After $Na_2WO_4.2H_2O$ (13.2 mg, 0.04 mmol), 36% hydrogen peroxide aqueous solution (290 mg, 3.0 mmol), methyltrioctylammonium chloride (8.1 mg, 0.02 mmol), and 3-cyclohexen-1-carboxylic acid allyl ester (333 mg, 2 mmol) were mixed, and were reacted at 25° C. for 15 min., the temperature was raised to 70° C., and the mixture was stirred for 2.5 hours. The same steps as in Example 1 were repeated. It was confirmed that the conversion rate of 3-cyclohexen-1-carboxylic acid allyl ester of a starting material was 0%, and the presence of 3,4-epoxycyclohexan-1-carboxylic acid allyl ester of a bifunctional epoxy monomer was not determined.

Comparative Example 2

After 36% hydrogen peroxide aqueous solution (400 mg, 4.2 mmol), methyltrioctylammonium hydrogen sulfate (15.6 mg, 0.033 mmol), and 3-cyclohexen-1-carboxylic acid allyl ester (670 mg, 4 mmol) were mixed, and were reacted at 25° C. for 15 min., the temperature was raised to 70° C., and the mixture was stirred for 3 hours. The same steps as in Example 1 were repeated. It was confirmed that the conversion rate of 3-cyclohexen-1-carboxylic acid allyl ester of a starting material was 0%, and the presence of 3,4-epoxycyclohexan-1-carboxylic acid allyl ester of a bifunctional epoxy monomer was not determined.

Comparative Example 3

After $Na_2WO_4.2H_2O$ (26.4 mg, 0.08 mmol), 36% hydrogen peroxide aqueous solution (400 mg, 4.2 mmol), and 3-cyclohexen-1-carboxylic acid allyl ester (670 mg, 4 mmol) were mixed, and were reacted at 25° C. for 15 min., the temperature was raised to 70° C., and the mixture was stirred for 3 hours. The same steps as in Example 1 were repeated. It was confirmed that the conversion rate of 3-cyclohexen-1-carboxylic acid allyl ester of a starting material was about 0%, and the presence of 3,4-epoxycyclohexan-1-carboxylic acid allyl ester of a bifunctional epoxy monomer was hardly determined.

The invention claimed is:

1. A method for producing a bifunctional epoxy monomer represented by the following formula (2):

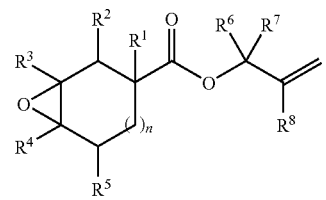

(2)

wherein n represents an integer of 0 to 2, $R^1$ to $R^8$ each is independently identical or different, and represents a hydrogen atom, a hydroxy group, a halogen atom, a carboxyl group, an alkyl group having 1 to 4 carbon atoms, an alkoxy group having 1 to 4 carbon atoms, a cycloalkyl group having 3 to 7 carbon atoms, an aryl group, an aralkyl group, an acyl group, an acyloxy group, or $R^1$ and $R^2$; $R^1$ and $R^3$; $R^1$ and $R^4$; $R^1$ and $R^5$; $R^2$ and $R^3$; $R^2$ and $R^4$; $R^2$ and $R^5$; $R^3$ and $R^4$; $R^3$ and $R^5$; or $R^4$ and $R^5$ represent a carbon chain bridge having 1 to 3 carbon atoms, and these groups may be independently substituted with an alkyl group having 1 to 4 carbon atoms, an alkoxy group having 1 to 4 carbon atoms, a cycloalkyl group having 3 to 7 carbon atoms, an aryl group, an aralkyl group, a carboxyl group or a halogen atom, the method comprising selectively oxidizing a diolefin compound represented by the following formula (1):

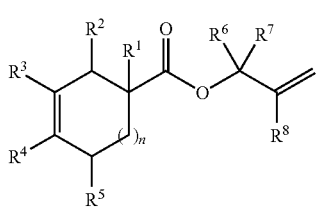

wherein n represents an integer of 0 to 2, $R^1$ to $R^8$ each is independently identical or different, and represents a hydrogen atom, a hydroxy group, a halogen atom, a carboxyl group, an alkyl group having 1 to 4 carbon atoms, an alkoxy group having 1 to 4 carbon atoms, a cycloalkyl group having 3 to 7 carbon atoms, an aryl group, an aralkyl group, an acyl group, an acyloxy group, or $R^1$ and $R^2$; $R^1$ and $R^3$; $R^1$ and $R^4$; $R^1$ and $R^5$; $R^2$ and $R^3$; $R^2$ and $R^4$; $R^2$ and $R^5$; $R^3$ and $R^4$; $R^3$ and $R^5$; or $R^4$ and $R^5$ represent a carbon chain bridge having 1 to 3 carbon atoms, and these groups may be independently substituted with an alkyl group having 1 to 4 carbon atoms, an alkoxy group having 1 to 4 carbon atoms, a cycloalkyl group having 3 to 7 carbon atoms, an aryl group, an aralkyl group, a carboxyl group or a halogen atom, using a hydrogen peroxide aqueous solution as an oxidizing agent without any use of an organic solvent, and using a Group VI metal compound and a quaternary ammonium hydrogen sulfate as a catalyst.

2. The method according to claim 1, wherein the reaction is performed at a temperature of 30 to 100° C.

3. The method according to claim 1, wherein said diolefin compound is selected from the group consisting of 3-cyclohexen-1-carboxylic acid allyl ester, 1-methyl-3-cyclohexen-1-carboxylic acid allyl ester, bicyclo[2.2.1]-5-hepten-2-methyl-2-carboxylic acid allyl ester, and 3-cyclohexen-1-carboxylic acid 2'-methyl-2'-propenyl ester.

4. The method according to claim 1, wherein said quaternary ammonium hydrogen sulfate is selected from the group consisting of tetrahexyammonium hydrogen sulfate, tetraoctylammonium hydrogen sulfate, and methyltrioctylammonium hydrogen sulfate.

5. The method according to claim 1, wherein said Group VI metal compound is selected from the group consisting of molybdic acid, molybdenum trioxide, phosphomolybdic acid, tungsten acid, tungsten trioxide, phosphotungstic acid, and sodium tungstate dihydrate.

6. The method according to claim 1, wherein said catalyst further comprises aminomethylphosphonic acid.

* * * * *

UNITED STATES PATENT AND TRADEMARK OFFICE
CERTIFICATE OF CORRECTION

| | | |
|---|---|---|
| PATENT NO. | : 7,696,366 B2 | Page 1 of 1 |
| APPLICATION NO. | : 11/914489 | |
| DATED | : April 13, 2010 | |
| INVENTOR(S) | : Hiroshi Uchida et al. | |

It is certified that error appears in the above-identified patent and that said Letters Patent is hereby corrected as shown below:

Item (73), on the Title Page, please insert --National Institute of Advanced Industrial Science and Technology--

Signed and Sealed this
Twenty-fifth Day of January, 2011

David J. Kappos
*Director of the United States Patent and Trademark Office*